US009061969B2

(12) United States Patent
Wu et al.

(10) Patent No.: US 9,061,969 B2
(45) Date of Patent: Jun. 23, 2015

(54) PHOTOLUMINESCENT ORGANIC MATERIAL

(75) Inventors: Jau-Yann Wu, Kaohsiung (TW);
Pei-Ying Tsai, Kaohsiung (TW);
I-Hsiang Wang, Kaohsiung (TW);
Shi-Xuan Chou, Kaohsiung (TW);
Guan-Ru Pan, Kaohsiung (TW);
Shih-Han Wang, Kaohsiung (TW);
Ting-Fan Chou, Kaohsiung (TW);
Ming-Yao Huang, Kaohsiung (TW);
Yu-Cheng Wang, Kaohsiung (TW)

(73) Assignee: I SHOU UNIVERSITY, Kaohsiung (TW)

( * ) Notice: Subject to any disclaimer, the term of this patent is extended or adjusted under 35 U.S.C. 154(b) by 845 days.

(21) Appl. No.: 13/289,130

(22) Filed: Nov. 4, 2011

(65) Prior Publication Data

US 2012/0267572 A1 Oct. 25, 2012

(30) Foreign Application Priority Data

Apr. 22, 2011 (TW) .............................. 100114068 A

(51) Int. Cl.
| | | |
|---|---|---|
| *C07F 7/04* | (2006.01) | |
| *C09K 11/06* | (2006.01) | |
| *C07C 251/08* | (2006.01) | |
| *A23L 1/30* | (2006.01) | |
| *C08B 31/00* | (2006.01) | |
| *C08B 37/08* | (2006.01) | |
| *C07F 15/00* | (2006.01) | |
| *C07F 15/02* | (2006.01) | |
| *C07F 15/04* | (2006.01) | |
| *C07F 15/06* | (2006.01) | |
| *C07F 1/00* | (2006.01) | |

(52) U.S. Cl.
CPC ............... *C07C 251/08* (2013.01); *A23L 1/30* (2013.01); *C08B 31/00* (2013.01); *C08B 37/003* (2013.01); *C09K 11/06* (2013.01); *C09K 2211/10* (2013.01); *C07F 15/004* (2013.01); *C07F 15/0053* (2013.01); *C07F 15/0093* (2013.01); *C07F 15/025* (2013.01); *C07F 15/045* (2013.01); *C07F 15/065* (2013.01); *C07F 1/005* (2013.01)

(58) Field of Classification Search
CPC .............................. C07F 15/0093; C08B 7/003

USPC ....................................... 252/301.16; 556/413
See application file for complete search history.

(56) References Cited

U.S. PATENT DOCUMENTS 6,476,268 B1 * 11/2002 Winsel et al. ................. 564/385

OTHER PUBLICATIONS

Bradley et al., J. Org. Chem. 2008, 73, 8673-8674.*
STIC STN Results—Best Art.*
Bradley et el., J. Org. Chem. 2008, 73, 8673-8674.*
Langer et al., Eur. J. Org. Chem. 2004, 1025-1032.*

* cited by examiner

*Primary Examiner* — Porfirio Nazario Gonzalez
*Assistant Examiner* — Kofi Adzamli
(74) *Attorney, Agent, or Firm* — Nixon & Vanderhye P.C.

(57) ABSTRACT

A compound of formula (I) is disclosed:

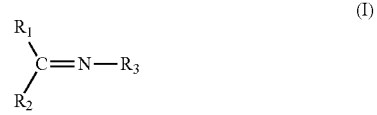

wherein definitions of $R_1$, $R_2$, and $R_3$ are the same as those defined in the specification. The compound of formula (I) can emit light via an intramolecular interaction of an imino group and an electron-donatable moiety contained in the compound.

A photoluminescent organic composition is also disclosed, which includes a compound represented by formula (II) in the presence of an electron-donatable compound,

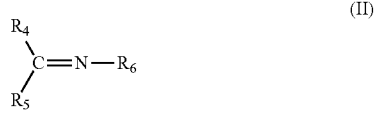

wherein definitions of $R_4$, $R_5$, and $R_6$ are the same as those defined in the specification. The photoluminescent organic composition can emit light via an intermolecular interaction of an imino group contained in the compound of formula (II) and an electron-donatable moiety contained in the electron-donatable compound.

11 Claims, 15 Drawing Sheets

PHOTOLUMINESCENT ORGANIC MATERIAL

CROSS-REFERENCE TO RELATED APPLICATION

This application claims priority of Taiwanese Application No. 100114068, filed Apr. 22, 2011.

BACKGROUND OF THE INVENTION

1. Field of the Invention

This invention relates to a photoluminescent compound, more particularly to a photoluminescent compound which emits light via an intramolecular interaction of an imino group and an electron-donatable moiety. This invention also relates to a photoluminescent organic composition which emits light via an intermolecular interaction of an imino group and an electron-donatable moiety.

2. Description of the Related Art

Fluorescence technique is being applied increasingly. With the assistance of fluorophores, many biological processes can be visualized at the molecular level. In recent years, there has been a dramatic proliferation of research concerned with the development of effective fluorescent materials. A wide variety of fluorescent species, such as organic dyes, metal-ligand complexes, quantum dots, and metal nanoclusters, have been synthesized, for a variety of applications.

Organic dyes are the molecules most commonly used as reporters in fluorescence sensing, due to their availability, low price, and versatility. However, the rapid photobleaching of the organic dyes limits the degree to which they can be practically applied. Additionally, the organic dyes usually contain lipophilic aryl rings, which have potential toxicity and which can not be easily applied in the biomedical field in which high hydrophilicity is desirable. Therefore, further processing is required to improve the hydrophilic property of the organic dyes.

Quantum dots and metal nanoclusters show greatly improved photostability, and are emerging as fluorescent reporters with properties and applications unavailable to traditional organic dyes. The performance of the quantum dots and the metal nanoclusters arise mainly from their unique size-dependent optical and electrical properties as the material-unit drops below a certain size. This size is typically between several to tens of nanometers for most of the quantum dots and only several to tens of atoms for the metal nanoclusters. In addition to optical properties and ultra small size, noble metal nanoclusters are highly attractive for biolabeling and bioimaging, due to their nontoxicity compared with the quantum dots.

Nonetheless, the severity of the size requirements pertaining to metal nanoclusters makes the preparation and long-term stability of these species a challenge that has greatly hampered studies of their fundamental properties, and investigations to broaden the range of available applications.

SUMMARY OF THE INVENTION

Therefore, an object of the present invention is to provide a photoluminescent organic material, which has satisfactory photoluminescence and photo-stability, and which can be reliably produced through a relatively simple process.

According to a first aspect of this invention, there is provided a compound of formula (I):

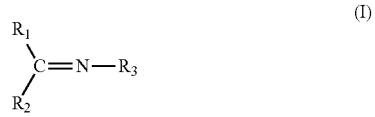

wherein at least one of $R_1$, $R_2$, and $R_3$ is a hetero-hydrocarbyl group containing an electron-donatable moiety, and the rest of $R_1$, $R_2$, and $R_3$ are independently a hydrocarbyl group. The compound of formula (I) can emit light via an intramolecular interaction of the imino group and the electron-donatable moiety contained in the compound.

According to a second aspect of this invention, there is provided a photoluminescent organic composition including a compound represented by formula (II) in the presence of an electron-donatable compound,

wherein $R_4$, $R_5$ and $R_6$ are independently a hydrocarbyl group or a hetero-hydrocarbyl group. The photoluminescent organic composition can emit light via an intermolecular interaction of the imino group contained in the compound of formula (II) and an electron-donatable moiety contained in the electron-donatable compound.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
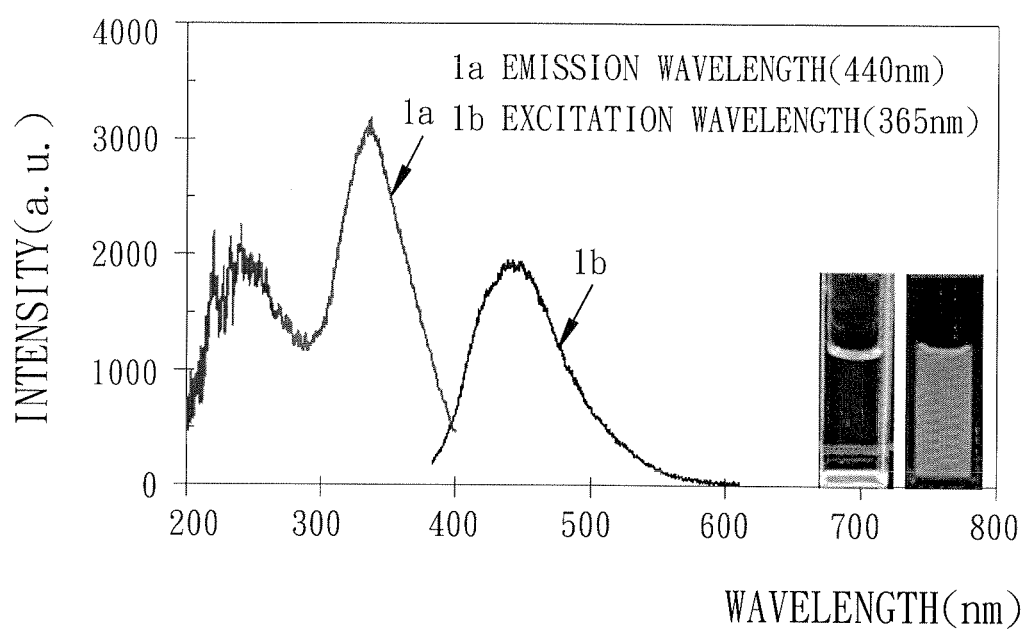
FIG. 1 is a fluorescent spectrogram illustrating the fluorescent analysis result of the organic photoluminescent material obtained in Example 1. Curve 1a represents an excitation spectrum at a wavelength of 440 nm. Curve 1b represents an emission spectrum at a wavelength of 365 nm. In the inset, the sample prior to ultraviolet irradiation and the sample after the ultraviolet irradiation at a wavelength of 365 nm are presented at the left and right sides of the inset, respectively.
Figure 2:
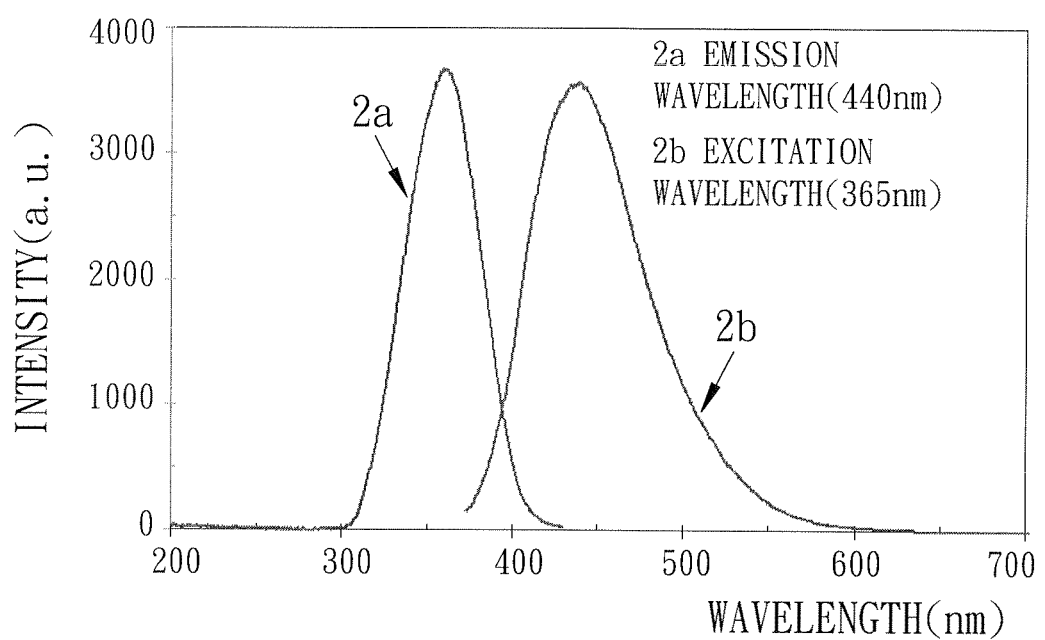
FIG. 2 is a fluorescent spectrogram illustrating the fluorescent analysis result of the organic photoluminescent material obtained in Example 2. Curve 2a represents an excitation spectrum at a wavelength of 440 nm. Curve 2b represents an emission spectrum at a wavelength of 365 nm.
Figure 3:
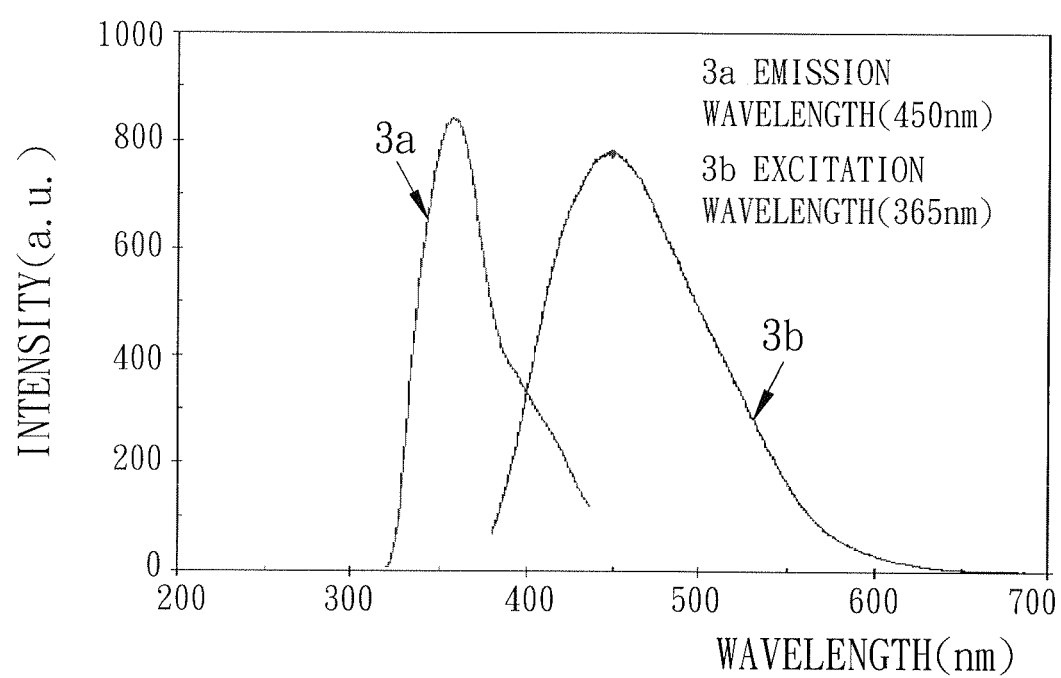
FIG. 3 is a fluorescent spectrogram illustrating the fluorescent analysis result of the organic photoluminescent material obtained in Example 3. Curve 3a represents an excitation spectrum at a wavelength of 450 nm. Curve 3b represents an emission spectrum at a wavelength of 365 nm.

The compound of the present invention is represented by formula (I):

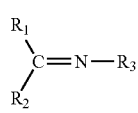

(I)

wherein at least one of $R_1$, $R_2$, and $R_3$ is a hetero-hydrocarbyl group containing an electron-donatable moiety, and the rest of $R_1$, $R_2$, and $R_3$ are independently a hydrocarbyl group. Furthermore, each of $R_1$, $R_2$, and $R_3$ is not an aryl group. Without wishing to be bound by any theory, it is believed that the compound of formula (I) emits light via an intramolecular interaction (for example, delocalization) of the imino group and the electron-donatable moiety contained in the compound. Since there is no aryl group in the compound of the present invention, satisfactory hydrophilicity can be possessed in the compound of the present invention so that the biocompatibility can be enhanced and the toxicity problem encountered in the prior art can be alleviated or eliminated when the compound of the present invention is used in the biomedical field.

The phrase "imino group" as used herein includes secondary ketimino group and secondary aldimino group.

The phrase "electron-donatable moiety" as used herein means an atom or functional group having lone-pair electrons. Examples of the electron-donatable moiety include, but are not limited to, electron-donatable atoms, such as an oxygen atom, a nitrogen atom, a sulfur atom, or the like; and electron-donatable groups, such as a hydroxyl group, an aldehyde group, a ketone group, an ether group, a siloxy group, an amino group, a thiol group, an amido group, or the like; and combinations thereof.

The compound of formula (I) of the present invention can be produced by:

(a) subjecting a starting compound to an intramolecular imine-formation reaction, wherein the starting compound contains the electron-donatable moiety, an amino group, and a reactive group capable of conducting the intramolecular imine-formation reaction with the amino group; or (b) subjecting a first compound and a second compound to an intermolecular imine-formation reaction, the first compound containing an amino group, the second compound containing a reactive group capable of conducting the intermolecular imine-formation reaction with the amino group of the first compound, at least one of the first compound and the second compound containing the electron-donatable moiety, the first compound and the second compound may be the same compound or different compounds.

Two of $R_1$, $R_2$, and $R_3$ form together a group containing a cyclic ring via the intramolecular imine-formation reaction.

When the compound of formula (I) is produced by the aforesaid reaction (a), the intramolecular imine-formation reaction is conducted in a solvent which can dissolve the starting material. Examples of the solvent suitable for the present invention include, but are not limited to, water, alcohol, ketone, ester, and combinations thereof.

Examples of the aforesaid reactive group contained in the starting compound include, but are not limited to, a hydroxyl group, an aldehyde group, a keto group, or the like.

Preferably, the starting compound is polyglucosamine. Examples of polyglucosamine include, but are not limited to, oligo-chitosan, chitosan, or the like. Oligo-chitosan or chitosan contains amino groups, aldose groups, and oxygen atoms in a same molecule. The aldose groups can conduct the intramolecular imine-formation reaction with the amino groups to form an imino group. The oxygen atoms are used as the electron-donatable moiety to conduct the intramolecular interaction with the produced imino group so as to emit light.

Preferably, the intramolecular imine-formation reaction is conducted at a temperature ranging from 25° C. to a reflux temperature of a combination of the starting compound and the solvent.

Preferably, a central metal is included to coordinate with the compound represented by formula (I) to form a complex. The complex is formed by adding a metal salt containing the metal during the intramolecular imine-formation reaction to conduct a coordination reaction. The metal salt is a salt of a metal selected from metals of Groups 8 to 11 in a Periodic Table of Elements. Any references to a Group or Groups shall be to the Group or Groups reflected in this Periodic Table of the Elements using the IUPAC (International Union of Pure and Applied Chemistry) system for numbering groups. Examples of the central metal include, but are not limited to, Fe, Ru, Os, Co, Rh, Ir, Ni, Pd, Pt, Cu, Au, and Ag. Examples of the metal salt include, but are not limited to, $AuCl_3$, $H_2PtCl_6 \cdot 6H_2O$, $CoCl_2 \cdot 6H_2O$, $IrCl_3$, $NiCl_2 \cdot 6H_2O$, $FeCl_3$, and $RuCl_3$.

Preferably, the coordination reaction to form the metal complex is conducted in a molar ratio of the metal salt to the starting compound ranging from 1:3 to 1:30.

In the metal complex containing the central metal and the compound of formula (I) as a ligand, light absorption and electron transportation can be enhanced by the central metal. Therefore, fluorescence can be improved and the range of light absorption wavelength can be expanded. The central metal contains metal nano-particles or metal nanoclusters. Preferably, the particle size of the central metal ranges from 0.2 to 2 nm.

When the compound of formula (I) is produced by the aforesaid reaction (b), the first compound containing an amino group is selected from monoamino alkane, diamino alkane, dialkyl amine, amino siloxane, amino acid, glucosamine, polyglucosamine, or combinations thereof. Alkyl group contained in the first compound has preferably from 1 to 20 carbon atoms, more preferably from 4 to 16 carbon atoms. Examples of polyglucosamine include, but are not limited to, oligo-chitosan, chitosan, or the like. The first compound used in the following illustrative examples includes 1-butylamine, 1-octylamine, 1-dodecylamine, 1-hexadecylamine, 1,6-hexadiamine, 3-aminopropyltriethoxysilane (APTES), and oligo-chitosan.

The reactive group contained in the second compound is a hydroxyl group, an aldehyde group, a keto group, or the like. The second compound is selected from aldehyde, ketone, alkyl alcohol, polyhydric alcohol, monosaccharide, polysaccharide, or combinations thereof.

Aldehyde or alkyl alcohol contains preferably from 1 to 10 carbon atoms, more preferably from 1 to 6 carbon atoms.

Ketone contains preferably from 2 to 10 carbon atoms, more preferably from 2 to 6 carbon atoms.

Polyhydric alcohol is an alcohol having two or more hydroxyl groups. Example of the polyhydric alcohol includes, but is not limited to, polyethylene glycol.

Examples of monosaccharide include, but are not limited to, glucose, glucosamine, fructose, or the like.

Polysaccharide is a reducing saccharide having two or more saccharide units. Examples of polysaccharide include, but are not limited to, glycosaminoglycan, acetyl glycosaminoglycan, maltose, dextrin, or the like. Examples of glycosaminoglycan include, but are not limited to, oligo-chitosan, chitosan, or the like. Examples of acetyl glycosaminoglycan include, but are not limited to, chitin, or the like.

The second compound used in the following illustrative examples includes acetone, methanol, ethanol, propanol, isopropanol, butanol, pentanol, hexanol, polyethylene glycol preferably having a molecular weight ranging from 5,000 to 7,000, oligo-chitosan, and water-soluble chitin.

It should be noted that a solvent can be used in the intermolecular imine-formation reaction, especially when the first compound and the second compound are both solid. Suitable solvent is one which is miscible with the first compound and the second compound, and examples thereof are the same as the aforesaid examples of the solvent suitable for the intra molecular imine-formation reaction.

Preferably, the intermolecular imine-formation reaction is conducted at a temperature ranging from 25° C. to a reflux temperature of a combination of the first compound and the second compound. Furthermore, the intermolecular imine-formation reaction is conducted at a molar ratio of the first compound to the second compound ranging preferably from 1:20,000 to 10:1.

Similarly, a metal salt can be added during the intermolecular imine-formation reaction so as to form a metal complex including a central metal and the compound of formula (I) as a ligand.

The compound of formula (I) produced via the intramolecular imine-formation reaction or the intermolecular imine-formation reaction can be further purified or formulated. The purification can be conducted via dialysis, chromatography, extraction, distillation, vacuum concentration, or the like.

The photoluminescent organic composition of the present invention includes a compound represented by formula (II) in the presence of an electron-donatable compound,

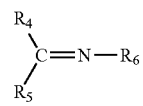

(II)

wherein $R_4$, $R_5$, and $R_6$ are independently a hydrocarbyl group or a hetero-hydrocarbyl group. Furthermore, each of $R_4$, $R_5$, and $R_6$ is not an aryl group.

Without wishing to be bound by any theory, it is believed that the photoluminescent organic composition emits light via an intermolecular interaction of the imino group contained in the compound of formula (II) and an electron-donatable moiety contained in the electron-donatable compound. Since there is no aryl group in the composition of the present invention, satisfactory hydrophilicity can be possessed in the composition of the present invention so that the biocompatibility can be enhanced and the toxicity problem encountered in the prior art can be alleviated or eliminated when the composition of the present invention is used in the biomedical field.

The electron-donatable compound is a compound containing an electron-donatable moiety selected from an oxygen atom, a nitrogen atom, a sulfur atom, a hydroxyl group, an aldehyde group, a ketone group, an ether group, a siloxy group, an amino group, a thiol group, an amido group, or combinations thereof.

The compound of formula (II) can be produced by:

(a') subjecting a starting compound to an intramolecular imine-formation reaction, wherein the starting compound contains an amino group, and a reactive group capable of conducting the intramolecular imine-formation reaction with the amino group; or (b') subjecting a first compound and a second compound to an intermolecular imine-formation reaction, the first compound containing an amino group, the second compound containing a reactive group capable of conducting the intermolecular imine-formation reaction with the amino group of the first compound, the first compound and the second compound may be the same compound or different compounds.

Two of $R_4$, $R_5$, and $R_6$ form together a group containing a cyclic ring via the intramolecular imine-formation reaction.

When the compound of formula (II) is produced by the aforesaid reaction (a'), the intramolecular imine-formation reaction is conducted in a solvent which can dissolve the starting material. Examples of the solvent suitable for the present invention include, but are not limited to, water, alcohol, ketone, ester, and combinations thereof.

Examples of the aforesaid reactive group contained in the starting compound include, but are not limited to, a hydroxyl group, an aldehyde group, a keto group, or the like.

Preferably, the starting compound is selected from glucosamine, polyglucosamine, or a combination thereof. Examples of polyglucosamine include, but are not limited to, oligo-chitosan, chitosan, or the like.

Preferably, the intramolecular imine-formation reaction is conducted at a temperature ranging from 25° C. to a reflux temperature of a combination of the starting compound and the solvent.

Preferably, a central metal is included to coordinate with the compound represented by formula (II) to form a complex. The complex is formed by adding a metal salt containing the metal during the intramolecular imine-formation reaction to conduct a coordination reaction. The metal salt is a salt of a metal selected from metals of Groups 8 to 11 in a Periodic Table of Elements. Examples of the central metal include, but are not limited to, Fe, Ru, Os, Co, Rh, Ir, Ni, Pd, Pt, Cu, Au, and Ag. Examples of the metal salt include, but are not limited to, $AuCl_3$, $H_2PtCl_6 \cdot 6H_2O$, $CoCl_2 \cdot 6H_2O$, $IrCl_3$, $NiCl_2 \cdot 6H_2O$, $FeCl_3$, and $RuCl_3$.

Preferably, the coordination reaction to form the metal complex is conducted in a molar ratio of the metal salt to the starting compound ranging from 1:3 to 1:30.

In the metal complex containing the central metal and the compound of formula (II) as a ligand, light absorption and electron transportation can be enhanced by the central metal. Therefore, fluorescence can be improved and the range of light absorption wavelength can be expanded. The central metal contains metal nano-particles or metal nanoclusters. Preferably, the particle size of the central metal ranges from 0.2 to 2 nm.

When the compound of formula (II) is produced by the aforesaid reaction (b'), the first compound containing an amino group is selected from monoamino alkane, diamino alkane, dialkyl amine, amino siloxane, amino acid, glucosamine, polyglucosamine, or combinations thereof. Alkyl group contained in the first compound has preferably from 1 to 20 carbon atoms, more preferably from 4 to 16 carbon atoms. Examples of polyglucosamine include, but are not limited to, oligo-chitosan, chitosan, or the like. The first compound used in the following illustrative examples includes 1-butylamine, 1-octylamine, 1-dodecylamine, 1-hexadecylamine, 1,6-hexadiamine, 3-aminopropyltriethoxysilane (APTES), and oligo-chitosan.

The reactive group contained in the second compound is a hydroxyl group, an aldehyde group, a keto group, or the like. The second compound is selected from aldehyde, ketone, alkyl alcohol, polyhydric alcohol, monosaccharide, polysaccharide, or combinations thereof.

Aldehyde or alkyl alcohol contains preferably from 1 to 10 carbon atoms, more preferably from 1 to 6 carbon atoms.

Ketone contains preferably from 2 to 10 carbon atoms, more preferably from 2 to 6 carbon atoms.

Polyhydric alcohol is an alcohol having two or more hydroxyl groups. Example of the polyhydric alcohol includes, but is not limited to, polyethylene glycol.

Examples of monosaccharide include, but are not limited to, glucose, glucosamine, fructose, or the like.

Polysaccharide is a reducing saccharide having two or more saccharide units. Examples of polysaccharide include, but are not limited to, glycosaminoglycan, acetyl glycosaminoglycan, maltose, dextrin, or the like. Examples of glycosaminoglycan include, but are not limited to, oligo-chitosan, chitosan, or the like. Examples of acetyl glycosaminoglycan include, but are not limited to, chitin, or the like.

The second compound used in the following illustrative examples includes acetone, methanol, ethanol, propanol, isopropanol, butanol, pentanol, hexanol, polyethylene glycol preferably having a molecular weight ranging from 5,000 to 7,000, oligo-chitosan, and water-soluble chitin.

Preferably, the intermolecular imine-formation reaction is conducted at a temperature ranging from 25° C. to a reflux temperature of a combination of the first compound and the second compound. Furthermore, the intermolecular imine-formation reaction is conducted at a molar ratio of the first compound to the second compound ranging preferably from 1:20,000 to 10:1.

It should be noted that the second compound remaining after the intermolecular imine-formation reaction can be used as the electron-donatable compound.

Similarly, a metal salt can be added during the intermolecular imine-formation reaction so as to form a metal complex including a central metal and the compound of formula (II) as a ligand.

As described above, the compound of formula (I) of the present invention can emit light via the intramolecular interaction of the imino group and the electron-donatable moiety contained in the compound, and the photoluminescent organic composition of the present invention can emit light via an intermolecular interaction of the imino group contained in the compound of formula (II) and an electron-donatable moiety contained in the electron-donatable compound. Furthermore, there is no aryl group in the compound of the present invention. Therefore, satisfactory hydrophilicity can be possessed in the compound or the photoluminescent organic composition of the present invention so that the biocompatibility can be enhanced and the toxicity problem encountered in the prior art can be alleviated or eliminated. The compound or the photoluminescent organic composition of the present invention can be used in the biomedical field, the photo-electric field, or the like.

The following examples are provided to illustrate the preferred embodiments of the invention, and should not be construed as limiting the scope of the invention.

EXAMPLES

Chemicals

The chemicals used in the following examples are listed in Table 1:

TABLE 1

|  | Chemicals | Descriptions | Suppliers |
|---|---|---|---|
| Metal salts | $AuCl_3$ | $AuCl_3$ | Acros |
|  | $IrCl_3 \cdot 3H_2O$ | $IrCl_3 \cdot 3H_2O$ | Acros |
|  | $H_2PtCl_6 \cdot 6H_2O$ | $H_2PtCl_6 \cdot 6H_2O$ | UniRegion Bio-Tech |
|  | $CoCl_2 \cdot 6H_2O$ | $CoCl_2 \cdot 6H_2O$ | Ishisu pharmaceutical |

TABLE 1-continued

| | Chemicals | Descriptions | Suppliers |
|---|---|---|---|
| | $NiCl_2 \cdot 6H_2O$ | $NiCl_2 \cdot 6H_2O$ | Nihon shiyaku industries |
| | $FeCl_3$ | $FeCl_3$ | Alfa Aesar |
| | $RuCl_3$ | $RuCl_3$ | Aldrich |
| Compounds containing an amino group | 1-butyl amine | $CH_3(CH_2)_3NH_2$ | Aldrich |
| | 1-octyl amine | $CH_3(CH_2)_7NH_2$ | Alfa Aesar |
| | 1-dodecyl amine | $CH_3(CH_2)_{11}NH_2$ | Alfa Aesar |
| | 1-hexadecyl amine | $CH_3(CH_2)_{15}NH_2$ | Aldrich |
| | 1,6-hexadi-amine | $H_2N(CH_2)_6NH_2$ | Alfa Aesar |
| Alcohols | 1-pentanol | $CH_3(CH_2)_4OH$ | Alfa Aesar |
| | 1-hexanol | $CH_3(CH_2)_5OH$ | Sigma-Aldrich |
| | 2-propanol | $CH_3CHOHCH_3$ | J. T. Baker |
| | Polyethylene glycol | MS: 5000~7000 | Riedel-de Haen |
| Ketones | Acetone | $CH_3COCH_3$ | J. T. Baker |
| Amino siloxane | APTES | $H_2N(CH_2)_3Si(OC_2H_5)_3$ | Aldrich |
| (Poly)saccharides | Oligo-chitosan | COS-KA Food grade, molecular weight: 400~2000; an oligomer containing 4-10 glucosamines | Lytone |
| | Water-soluble chitin | Food grade, an oligomer containing 2-6 repeating units | Lytone |
| | D(+)-maltose monohydrate | $C_{12}H_{22}O_{11} \cdot H_2O$ | Acros Organics |
| | dextrin | Glucose oligomer | Nihon Shiyaku Industies |

Example 1

50 mg of oligo-chitosan and 50 ml of water were mixed at room temperature to obtain a mixture. The mixture was stirred at 90° C. to conduct an imine-formation reaction for 48 hours. A photoluminescent compound was obtained after removing water.

Examples 2 to 21

The first compound and the second compound for the aforesaid intermolecular imine-formation reaction are listed in Table 2. The optional metal salts and solvent, and the conditions for the intermolecular imine-formation reaction are also listed. The first compound, the second compound, and the optional metal salt and solvent were mixed at room temperature to obtain a mixture. The intermolecular imine-formation reaction was conducted by stirring the mixture at conditions listed in Table 2 to obtain photoluminescent materials.

In Examples 2-14 and 17-21, the second compounds, such as pentanol, acetone, isopropanol, hexanol, polyethylene glycol, oligo-chitosan, water-soluble chitin, maltose, and dextrin, contain the electron-donatable moiety. It should be noted that, for example, in Examples 2 and 3, the second compounds (i.e., pentanol and acetone) are stoichiometrically excess relative to the first compounds. Therefore, the second compounds in Examples 2 and 3 are used as the solvent for the intermolecular imine-formation reaction and as the compound providing the electron-donatable moiety for the intermolecular interaction with the products containing imine group so as to emit light. In Examples 4-13 and 17, metal salts are used so as to form metal complexes. In Example 15, the first compound contains the electron-donatable moiety. In Example 16, both the first compound and the second compound contain the electron-donatable moiety.

TABLE 2

| Ex. | First compound[1] (µmol) | Second compound[2] (µmol; ml or g) | Metal salt (µmol) | Solvent (ml) | Temp. (° C.) | Time (h) |
|---|---|---|---|---|---|---|
| 2 | 1-dodecylamine (90) | Pentanol (276350; 30 ml) | — | — | 90 | 288 |
| 3 | 1-butylamine (300) | Acetone (409350; 20 ml) | — | — | 60 | 24 |
| 4 | 1-dodecylamine (42) | Pentanol (138175; 15 ml) | $H_2PtCl_6 \cdot 6H_2O$ (7) | — | 90 | 12 |
| 5 | 1-dodecylamine (42) | Pentanol (138175; 15 ml) | $CoCl_2 \cdot 6H_2O$ (7) | — | 90 | 160 |
| 6 | 1-dodecylamine (42) | Pentanol (138175; 15 ml) | $IrCl_3$ (7) | — | 90 | 12 |
| 7 | 1-dodecylamine (42) | Pentanol (138175; 15 ml) | $NiCl_2 \cdot 6H_2O$ (7) | — | 90 | 86 |
| 8 | 1-butylamine (42) | Isopropanol (65310; 5 ml) | $AuCl_3$ (7) | Water (10) | 60 | 72 |
| 9 | 1-octylamine (42) | Isopropanol (65310; 5 ml) | $AuCl_3$ (7) | Water (10) | 60 | 72 |
| 10 | 1-dodecylamine (42) | Isopropanol (65310; 5 ml) | $AuCl_3$ (7) | Water (10) | 60 | 72 |
| 11 | 1-hexadecylamine (42) | Isopropanol (65310; 5 ml) | $AuCl_3$ (7) | Water (10) | 60 | 72 |
| 12 | 1,6-hexadiamine (42) | Pentanol (138175; 15 ml) | $FeCl_3$ (7) | — | 120 | 96 |
| 13 | 1-octylamine (2.3) | Hexanol (39835; 5 ml) | $RuCl_3$ (7) | Water (10) | 90 | 120 |
| 14 | 1-dodecylamine (42) | Polyethylene glycol (750; 4.5 g) | — | Water (15) | 90 | 24 |
| 15 | APTES (2100) | Acetone (955175; 70 ml) | — | — | 50 | 48 |
| 16 | Oligo-chitosan (30 mg) | Acetone (102340; 7.5 ml) | — | Water (7.5) | 50 | 48 |
| 17 | 1-butylamine (225) | Oligo-chitosan (0.03 g) | — | Water (7.5) | 60 | 24 |
| 18 | 1-butylamine (225) | Water-soluable chitin (0.03 g) | — | Water (15) | 90 | 24 |
| 19 | 1-butylamine (300) | Maltose (50 µmol) | — | Water (50) | 90 | 21 |
| 20 | 1-butylamine (150) | Dextrin (0.1 g) | — | Water (50) | 90 | 21 |
| 21 | 1-dodecylamine (42) | Pentanol (46058; 5 ml) | $AuCl_3$ (7) | Water (10) | 60 | 72 |

[1]The first compound is a compound containing an amino group.

[2]The second compound is a compound containing a reactive group capable of conducting an intermolecular imine-formation reaction with the amino group of the first compound.

Figure 4:
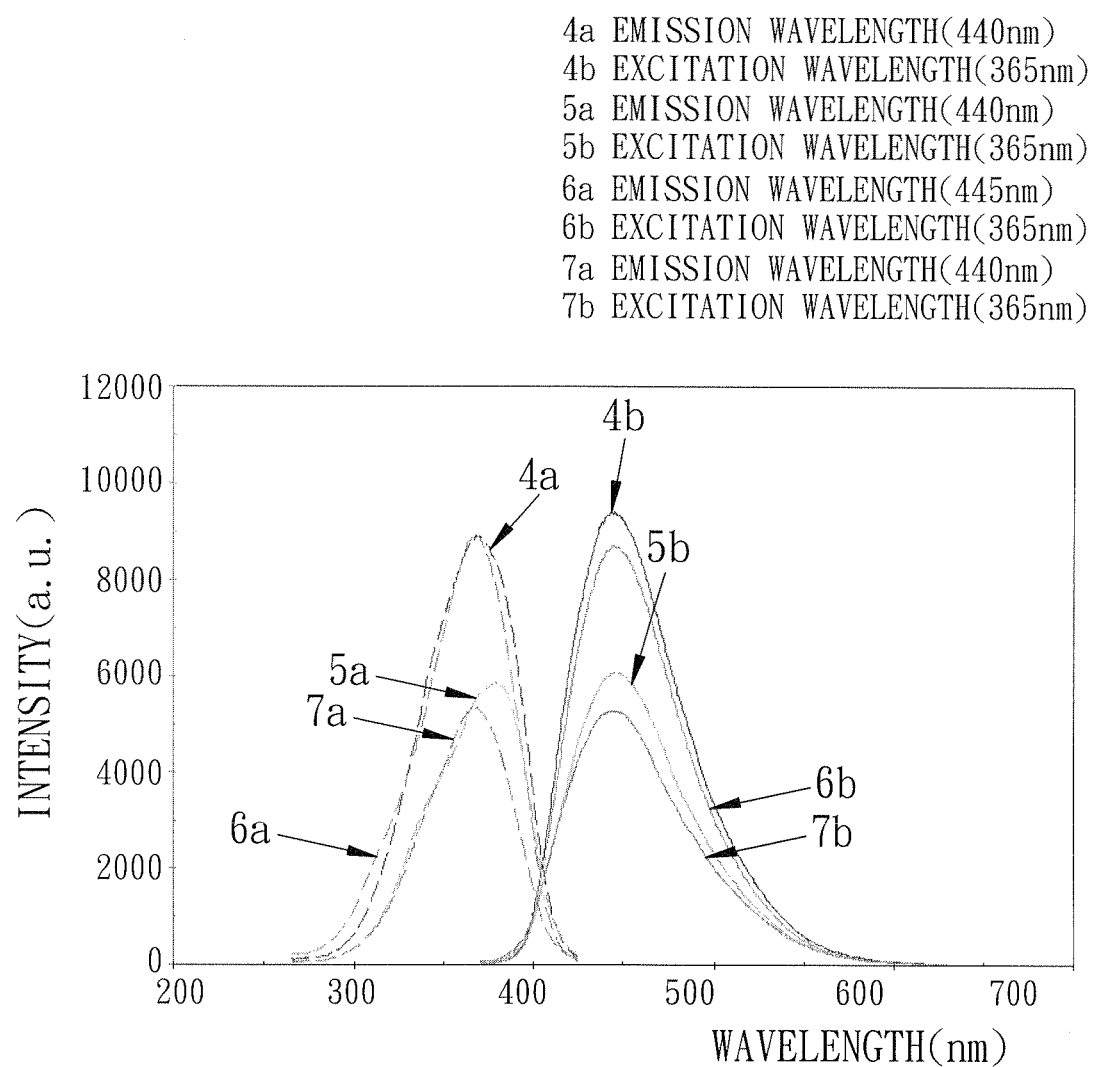
FIG. 4 is a fluorescent spectrogram illustrating the fluorescent analysis result of the organic photoluminescent materials obtained in Examples 4 to 7. Curves 4a to 7a represent excitation spectra at a wavelength of 440 or 445 nm. Curves 4b to 7b represent emission spectra at a wavelength of 365 nm.
Figure 5:
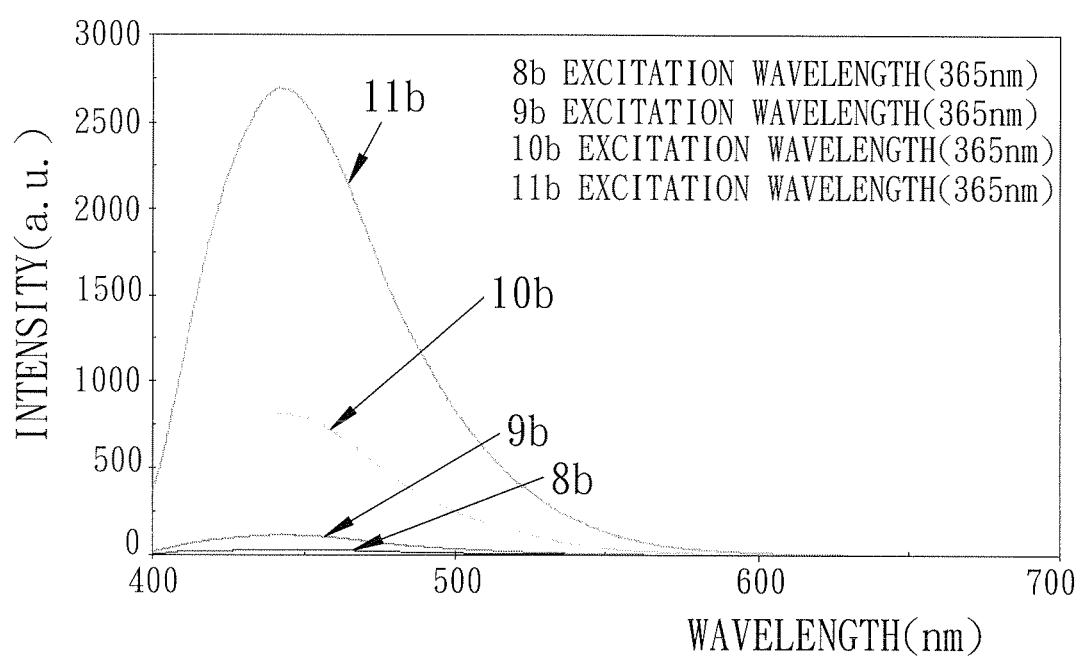
FIG. 5 is a fluorescent spectrogram illustrating the fluorescent analysis result of the organic photoluminescent materials obtained in Examples 8 to 11. Curves 8b to 11b represent emission spectra at a wavelength of 365 nm.
Figure 6:
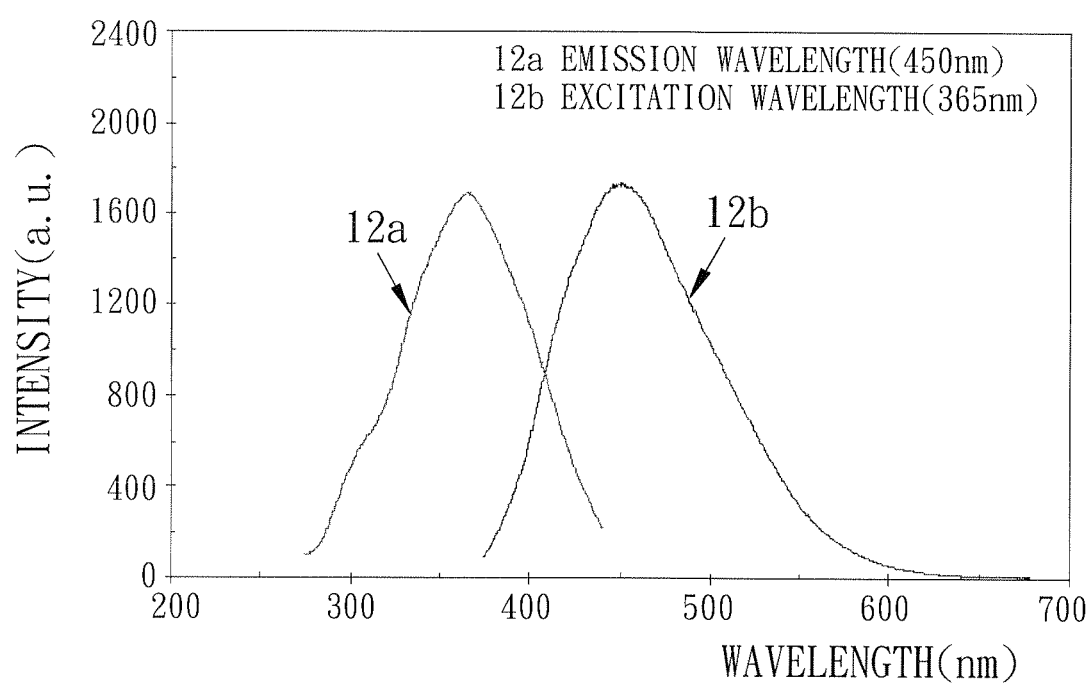
FIG. 6 is a fluorescent spectrogram illustrating the fluorescent analysis result of the organic photoluminescent material obtained in Example 12. Curve 12*a* represents an excitation spectrum at a wavelength of 450 nm. Curve 12*b* represents an emission spectrum at a wavelength of 365 nm.
Figure 7:
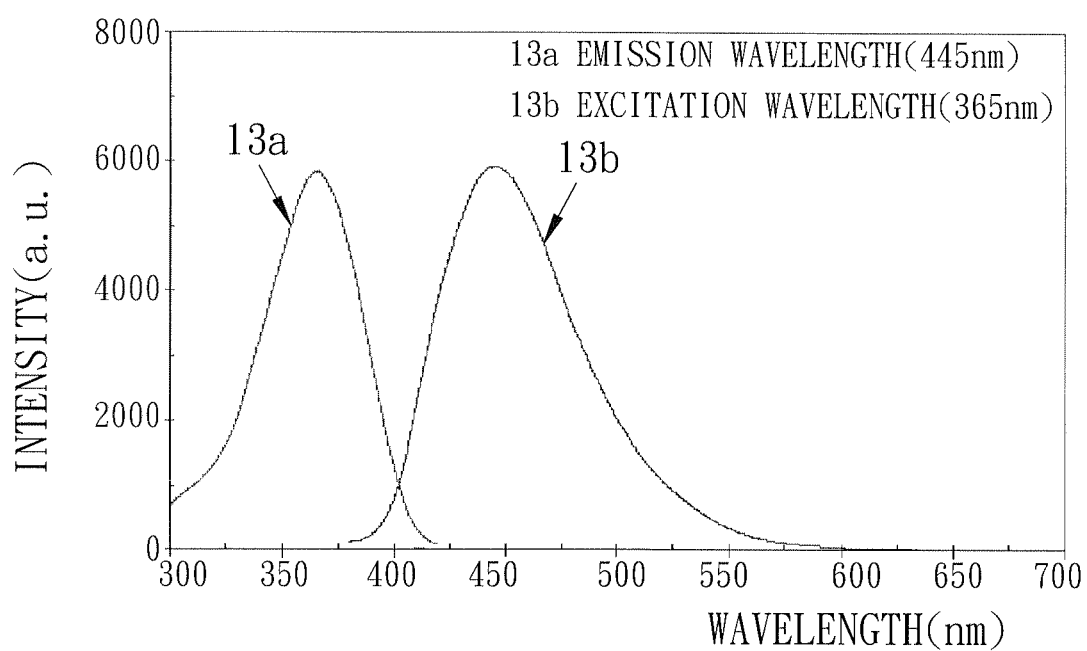
FIG. 7 is a fluorescent spectrogram illustrating the fluorescent analysis result of the organic photoluminescent material obtained in Example 13. Curve 13*a* represents an excitation spectrum at a wavelength of 445 nm. Curve 13*b* represents an emission spectrum at a wavelength of 365 nm.
Figure 8:
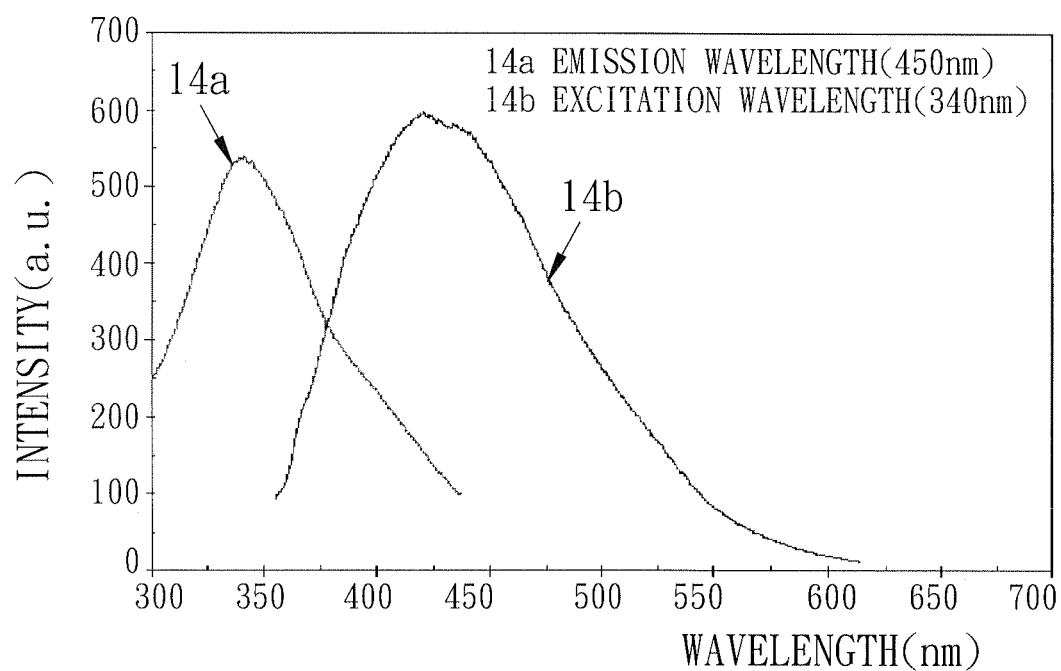
FIG. 8 is a fluorescent spectrogram illustrating the fluorescent analysis result of the organic photoluminescent material obtained in Example 14. Curve 14*a* represents an excitation spectrum at a wavelength of 450 nm. Curve 14*b* represents an emission spectrum at a wavelength of 340 nm.
Figure 9:
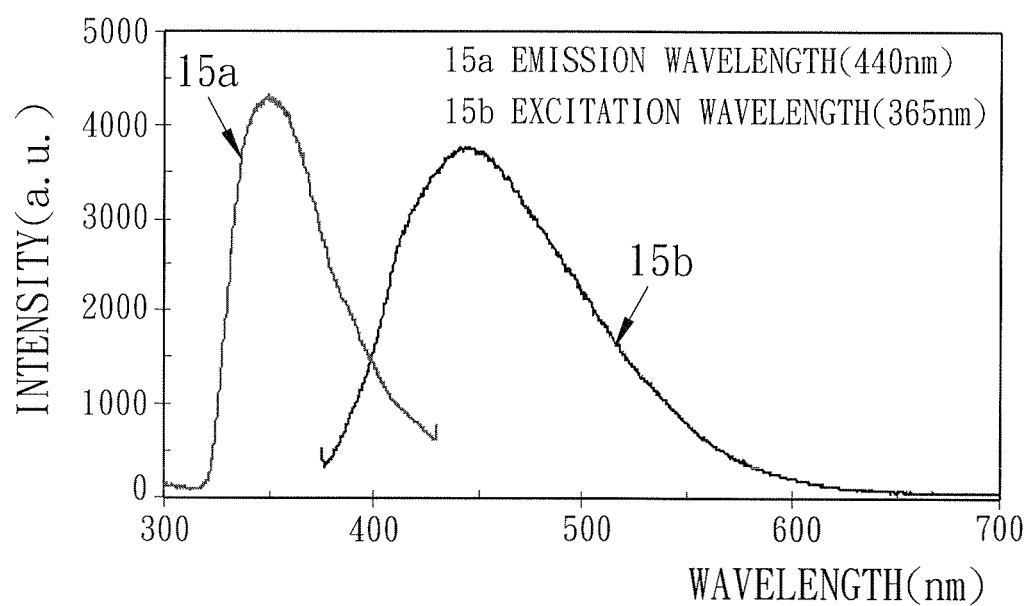
FIG. 9 is a fluorescent spectrogram illustrating the fluorescent analysis result of the organic photoluminescent material obtained in Example 15. Curve 15*a* represents an excitation spectrum at a wavelength of 440 nm. Curve 15*b* represents an emission spectrum at a wavelength of 365 nm.
Figure 10:
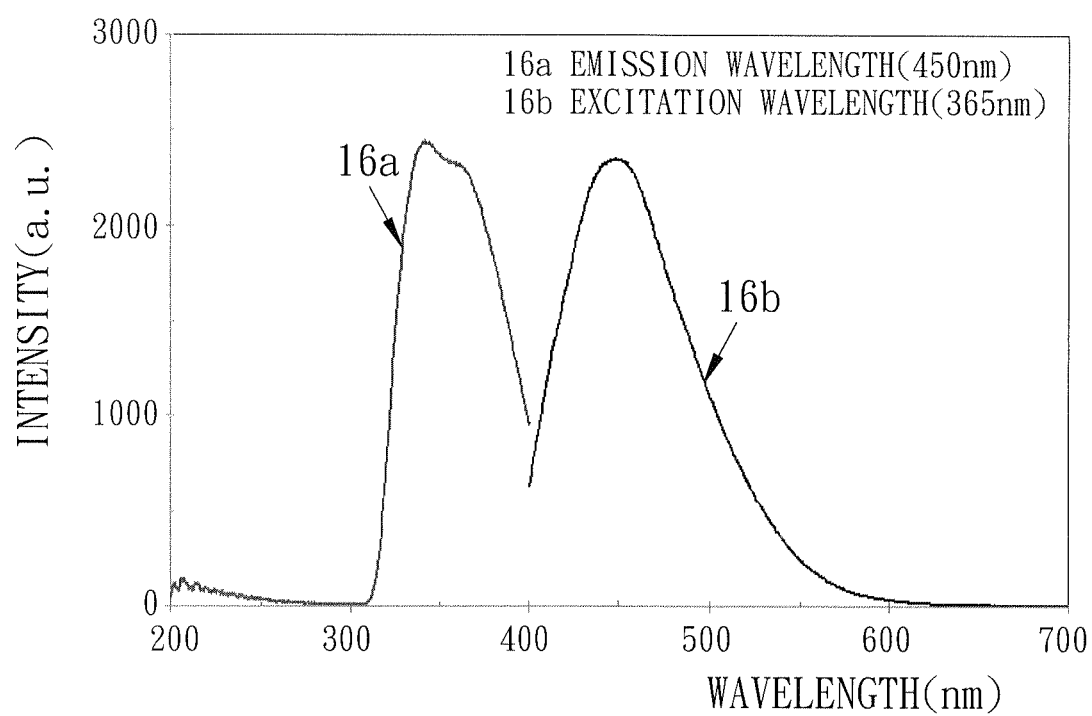
FIG. 10 is a fluorescent spectrogram illustrating the fluorescent analysis result of the organic photoluminescent material obtained in Example 16. Curve 16*a* represents an excitation spectrum at a wavelength of 450 nm. Curve 16*b* represents an emission spectrum at a wavelength of 365 nm.
Figure 11:
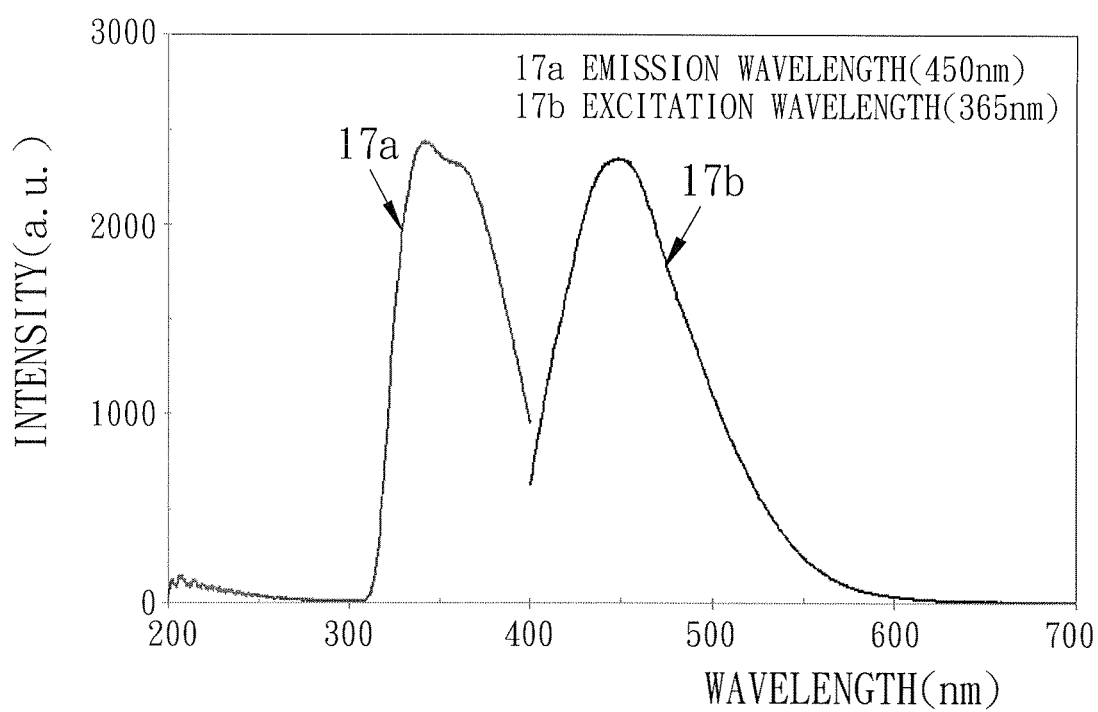
FIG. 11 is a fluorescent spectrogram illustrating the fluorescent analysis result of the organic photoluminescent material obtained in Example 17. Curve 17*a* represents an excitation spectrum at a wavelength of 450 nm. Curve 17*b* represents an emission spectrum at a wavelength of 365 nm.
Figure 12:
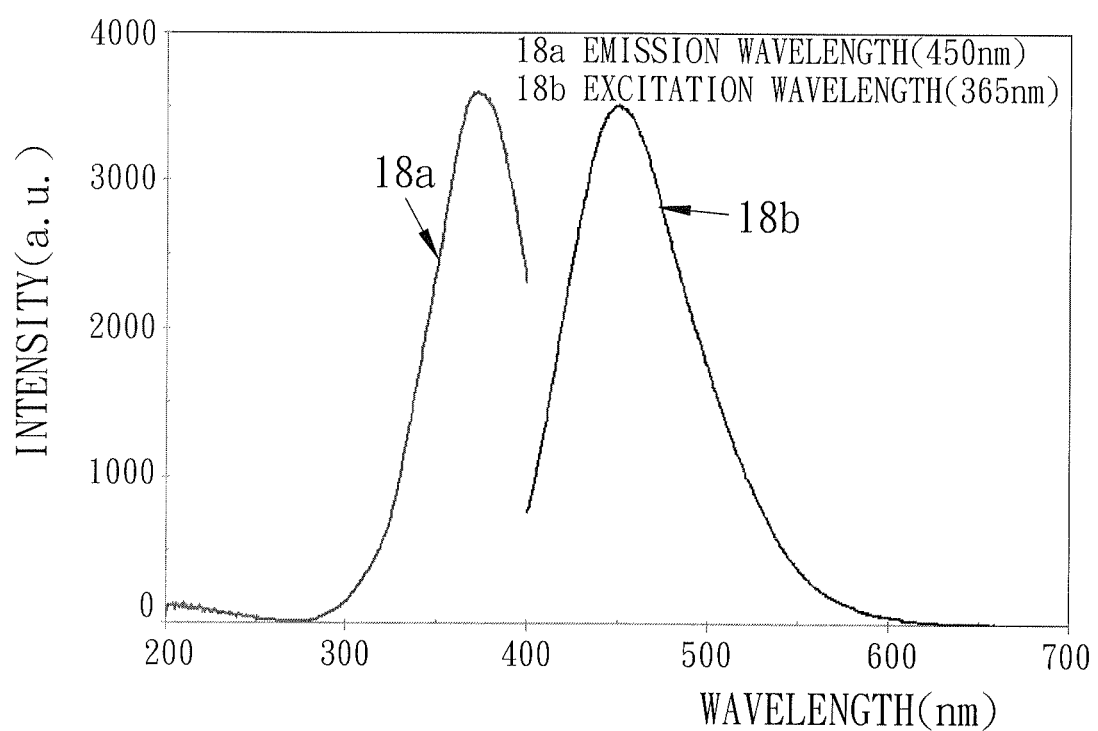
FIG. 12 is a fluorescent spectrogram illustrating the fluorescent analysis result of the organic photoluminescent material obtained in Example 18. Curve 18*a* represents an excitation spectrum at a wavelength of 450 nm. Curve 18*b* represents an emission spectrum at a wavelength of 365 nm.
Figure 13:
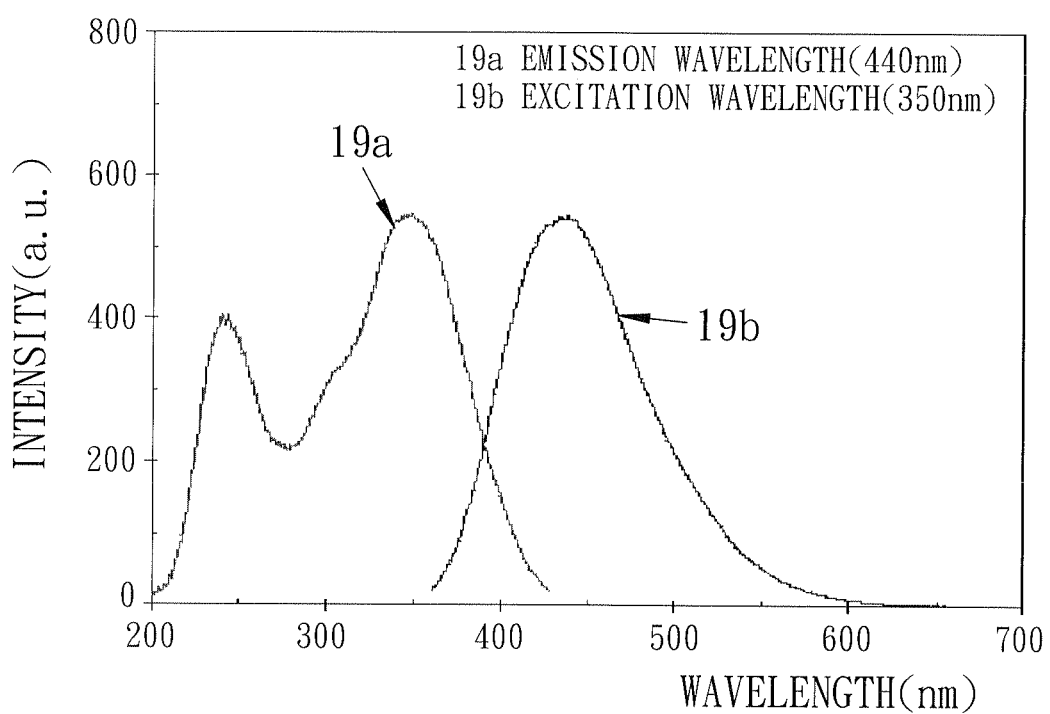
FIG. 13 is a fluorescent spectrogram illustrating the fluorescent analysis result of the organic photoluminescent material obtained in Example 19. Curve 19*a* represents an excitation spectrum at a wavelength of 440 nm. Curve 19*b* represents an emission spectrum at a wavelength of 365 nm.
Figure 14:
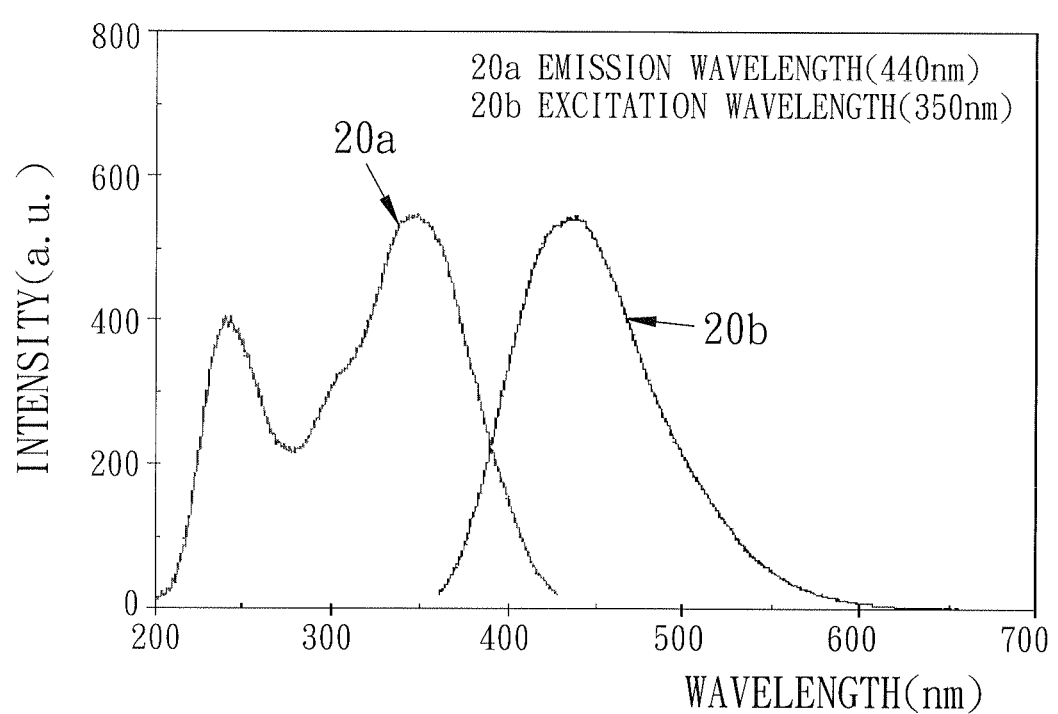
FIG. 14 is a fluorescent spectrogram illustrating the fluorescent analysis result of the organic photoluminescent material obtained in Example 20. Curve 20*a* represents an excitation spectrum at a wavelength of 440 nm. Curve 20*b* represents an emission spectrum at a wavelength of 350 nm.

Fluorescence Analysis:

Excitation and emission spectra of the photoluminescent materials obtained in Examples 1-21 were analyzed using a fluorescence spectrophotometer (manufactured by Hitachi, Model No. F-4500). The results are shown in FIGS. 1 to 15, in which the letter "a" represents an excitation spectrum, and the letter "b" represents an emission spectrum. The results of Examples 4 to 7 are shown in FIG. 4. The results of Examples 8 to 11 are shown in FIG. 5.

As shown in FIGS. 1 to 15, all of the products obtained in Examples 1 to 21 emit blue fluorescence. Furthermore, although the optimal excitation wavelength or the optimal emission wavelength may be different, all of the products obtained in Examples 1 to 21 can emit satisfactory fluorescence.

Fluorescence Stability Analysis:

The product obtained in Example 21 was used for the fluorescence stability analysis. The product was centrifuged at 11,000 rpm to remove particles remained in the product, and was then dried via vacuum concentration to obtain a test sample. The test sample was exposed using an ultraviolet light of 12 watts at a distance of 10 cm from the test sample for 15 hours. The fluorescence intensity (excitation wavelength: 365 nm) was determined using a fluorescence spectrophotometer for every 5 hours. The result is shown in FIG. 15.

Figure 15:
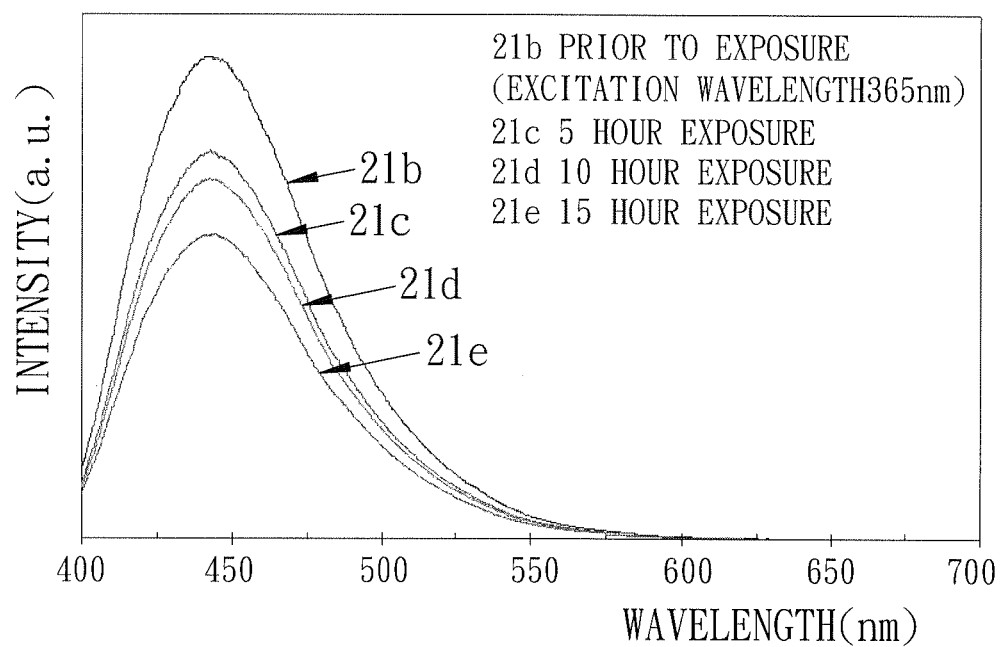
FIG. 15 is a fluorescent spectrogram illustrating the fluorescent analysis result of the organic photoluminescent material obtained in Example 21. Curve 21*b* represents an emission spectrum at a wavelength of 365 nm. Curve 21*c* represents an emission spectrum after ultraviolet irradiation of 5 hours. Curve 21*d* represents an emission spectrum after ultraviolet irradiation of 10 hours. Curve 21*e* represents an emission spectrum after ultraviolet irradiation of 15 hours.

As shown in FIG. 15, although the fluorescence intensity was slightly reduced with the passage of time, the product obtained in Example 15 still retains a fluorescence intensity which is satisfactory for the art.

In view of the aforesaid, the photoluminescent organic material of the present invention can emit light via the interaction of an imino group and an electron-donatable moiety contained therein. As shown above, the photoluminescent organic material of the present invention has satisfactory fluorescence intensity and stability. Furthermore, there is no aryl group in the photoluminescent organic material of the present invention so that the biocompatibility can be enhanced and the toxicity problem encountered in the prior art can be alleviated or eliminated when used in the biomedical field.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A photoluminescent compound of formula (I):

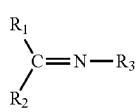

(I)

wherein at least one of $R_1$, $R_2$, and $R_3$ is a hetero-hydrocarbyl group containing an electron-donatable moiety, and the rest of $R_1$, $R_2$, and $R_3$ are independently a hydrocarbyl group, wherein each of $R_1$, $R_2$, and $R_3$ is not an aryl group, and wherein said electron-donatable moiety provides donatable electrons to interact with an imino group contained in said compound of formula (I) so as to permit said compound of formula (I) to emit light.

2. The photoluminescent compound as claimed in claim 1, wherein said electron-donatable moiety is selected from a group consisting of an oxygen atom, a nitrogen atom, a sulfur atom, a hydroxyl group, an aldehyde group, a ketone group, an ether group, a siloxy group, an amino group, a thiol group, an amido group, and combinations thereof.

3. The photoluminescent compound as claimed in claim 1, which is produced by
   (a) subjecting a starting compound to an intramolecular imine-formation reaction, wherein said starting compound contains said electron-donatable moiety, an amino group, and a reactive group capable of conducting said intramolecular imine-formation reaction with said amino group; or
   (b) subjecting a first compound and a second compound to an intermolecular imine-formation reaction, said first compound containing an amino group, said second compound containing a reactive group capable of conducting said intermolecular imine-formation reaction with said amino group of said first compound, at least one of said first compound and said second compound containing said electron-donatable moiety, said first compound and said second compound may be the same compound or different compounds.

4. The photoluminescent compound as claimed in claim 3, wherein said starting compound is polyglucosamine.

5. The photoluminescent compound as claimed in claim 3, wherein said intramolecular imine-formation reaction is conducted in a solvent selected from a group consisting of water, alcohol, ketone, ester, and combinations thereof.

6. The photoluminescent compound as claimed in claim 5, wherein said intramolecular imine-formation reaction is conducted at a temperature ranging from 25° C. to a reflux temperature of a combination of said starting compound and said solvent.

7. The photoluminescent compound as claimed in claim 3, wherein said first compound is selected from a group consisting of monoamino alkane, diamino alkane, dialkyl amine, amino siloxane, amino acid, glucosamine, polyglucosamine, and combinations thereof, and said second compound is selected from a group consisting of aldehyde, ketone, alkyl alcohol, polyhydric alcohol, monosaccharide, polysaccharide, and combinations thereof.

8. The photoluminescent compound as claimed in claim 3, wherein said intermolecular imine-formation reaction is conducted at a temperature ranging from 25° C. to a reflux temperature of a combination of said first compound and said second compound.

9. The photoluminescent compound as claimed in claim 3, wherein two of $R_1$, $R_2$, and $R_3$ form together a group containing a cyclic ring via said intramolecular imine-formation reaction.

10. The photoluminescent compound as claimed in claim 1, further comprising a central metal which is capable of coordinating with said compound represented by formula (I) to form a complex.

11. The photoluminescent compound as claimed in claim 10, wherein said central metal is selected from metals of Groups 8 to 11 in a Periodic Table of Elements.

* * * * *